United States Patent
Hain et al.

(10) Patent No.: US 8,171,771 B2
(45) Date of Patent: May 8, 2012

(54) CALIBRATION FOR A NONDESTRUCTIVE MATERIAL TESTING SYSTEM

(75) Inventors: Stefan Hain, Effeltrich (DE); Hubert Mooshofer, Munich (DE); Fabricio de Carvalho Ferreira, Munich (DE)

(73) Assignee: Siemens Aktiengesellschaft, Munich (DE)

( * ) Notice: Subject to any disclaimer, the term of this patent is extended or adjusted under 35 U.S.C. 154(b) by 444 days.

(21) Appl. No.: 12/407,154

(22) Filed: Mar. 19, 2009

(65) Prior Publication Data

US 2009/0282895 A1 Nov. 19, 2009

(30) Foreign Application Priority Data

Mar. 25, 2008 (DE) .................. 10 2008 015 495

(51) Int. Cl.
*G01V 13/00* (2006.01)
*G01N 29/04* (2006.01)
(52) U.S. Cl. .......................... 73/1.82; 73/641
(58) Field of Classification Search ............... 73/1.82
See application file for complete search history.

(56) References Cited

U.S. PATENT DOCUMENTS

| | | | |
|---|---|---|---|
| 3,898,838 A | 8/1975 | Connelly | 73/67.8 |
| 4,170,891 A | 10/1979 | Elsner | 73/1.83 |
| 4,354,388 A * | 10/1982 | Diepers et al. | 73/612 |
| 6,182,494 B1 * | 2/2001 | Reed et al. | 73/1.83 |
| 6,220,099 B1 | 4/2001 | Marti et al. | 73/633 |
| 7,181,970 B2 * | 2/2007 | Haase et al. | 73/621 |

FOREIGN PATENT DOCUMENTS

| | | |
|---|---|---|
| DE | 103 49 948 B3 | 1/2005 |
| EP | 0060952 A2 | 9/1982 |
| GB | 2015740 A | 9/1979 |

OTHER PUBLICATIONS

G.P.P. Gunarathne and Y. Qureshi; A Novel Technique for Dynamic Alignment of Ultrasonic Transducers in Real-time Non\-destructive Testing; May 20-22, 2003; IEEE Instrumentation and Measurement Technology Conference.*
Gunarathne, et al., "A Novel Technique for Dynamic Alignment of Ultrasonic Transducers in Real-time Non-destructive Testing", IEEE Instrumentation and Measurement Technology Conference, pp. 1137-1142, May 20, 2003.
German Office action, German application No. 10 2008 015 495.4-52, 4 pages, Sep. 30, 2008.
Zhenqi Zhu et al. "Calibration of Laser Displacement Sensor Used by Industrial Robots" Optical Engineering, vol. 43, No. 1 (2 pages), Jan. 2004.

* cited by examiner

*Primary Examiner* — Hezron E Williams
*Assistant Examiner* — Gregory J Redmann
(74) *Attorney, Agent, or Firm* — King & Spalding L.L.P.

(57) ABSTRACT

Calibration for a nondestructive ultrasonic material testing system is provided, the system having a multiplicity of ultrasound transducers which are linearly movable as a whole but are arranged fixed with respect to one another, for example mounted fixed in a single sensor holder. In order to achieve optimal alignment of the sensors with a specimen, the mechanical tolerance-induced offset between the beam direction of the ultrasound transducers and the ideal beam directions is found, for example with the aid of a mean straight line. It is then minimized by using the available degrees of freedom of the sensor holder, for example possible tilting of the sensor holder.

11 Claims, 2 Drawing Sheets

CALIBRATION FOR A NONDESTRUCTIVE MATERIAL TESTING SYSTEM

CROSS-REFERENCE TO RELATED APPLICATIONS

This application claims priority to German patent application No. 10 2008 015 495.4, filed Mar. 25, 2008. The complete disclosure of the above-identified priority application is hereby fully incorporated herein by reference.

TECHNICAL FIELD

The invention relates to the field of nondestructive material testing. For this, there are a range of possibilities. For example radiation from a specimen to be tested, for example thermal radiation, may be received and evaluated using sensors. In this case, for example, the surface of the specimen is scanned. It is also possible to emit the radiation and then to receive and evaluate a reflected fraction of this radiation. The radiation may be electromagnetic radiation or sound waves, for example ultrasound. The invention deals in particular with an ultrasound transducer system, although it may also be used for other types of radiation. In the rest of the text, the term transducer will be used for a respective sensor or a combination of a sensor and an emitter for the radiation. For example, ultrasound transducer may refer to an ultrasound sensor or a combination of an ultrasound transmitter and an ultrasound receiver.

BACKGROUND

Depending on the radiation being used, it may be necessary to maintain a particular distance of the transducer or transducers from the surface of the specimen. Furthermore, depending on the type of radiation being used, it may be necessary to maintain a particular angle with respect to the surface of the specimen. The required precision is commensurately higher when the surface curvature on the specimen is greater and the focusing of the transducers being used is stronger.

Arrangements consisting of a plurality of transducers are used for many testing tasks, for example searching for defects of different orientation, or to accelerate the test by testing a plurality of sites simultaneously. The transducers must in this case be precisely positioned and aligned with respect to one another, especially when the measurement positions need to be partially assigned to the transducers for precise defect localization, when there is a strong surface curvature and when using focused transducers, and/or when testing a plurality of sites simultaneously.

In practice, manufacturing tolerances and deviations occur when using the transducers, as below with reference to the example of ultrasound transducers:

The outgoing sound beam is not exactly concentric. Real sound transducers have offset and angle errors of the sound beam in relation to the nominal axis;

According to the manufacturing tolerances, the time of flight origin point of the sound varies in relation to the reference edge of the transducer, for example an endstop on the front edge;

Owing to housing tolerances, variations of the transducer positioning may take place, for example lateral offset in the event of diameter variations. The transducers may be displaced in the longitudinal direction owing to imprecise fitting. The transducer positioning may change after replacement of a transducer.

In the case of a plurality of sensors mounted on a common holder, an individually different error is encountered for each sensor. Even when a highly precise mechanism is employed for positioning and aligning the sensor holder, the accuracy with which the individual sensors are aligned is insufficient.

It is known to carry out the sensor positioning by mechanical contact with the surface, for example using rolls and slight pressure by means of a spring force. When using a plurality of sound transducers, the sensor frame may be configured in multiple parts so that each transducer is separately guided and positioned by the pressure on the surface. A disadvantage with this is that precise guiding by rolls is not possible for surfaces with a strong and varying curvature.

Furthermore, exact spatial assignment of the measurements is not possible when the transducers can move without measurement of the relative position, although this is scarcely still practicable even with two transducers. A disadvantage with guiding by rolls is furthermore the mechanical stress on the specimen surface, or the scanning speed limitation required in order to avoid damage or wear. Furthermore, guiding by rolls is scarcely practicable in the immersion technique.

The manufacturing tolerances can be reduced through selection of the transducers. Some of said error effects can thereby be reduced. A disadvantage with this is that only a limited improvement can be achieved. Another disadvantage is that a greater number of transducers are used according to the degree of selection, particularly when the transducers are selected in relation to a plurality of types of manufacturing tolerances, for example offset, tilt of the sound beam, diameter.

As an alternative to a rigid sensor holder in which all the sound transducers are fitted in a fixed fashion, a sensor holder may be designed with adjusters. A disadvantage, however, is that one adjuster for offset and another for the tilt must be provided for each sound transducer, so that the emitted sound beams of the transducers can be adjusted according to the desired setpoint alignment. The outlay and space requirement necessary for this are scarcely practicable. Under certain circumstances, in the case of a compact transducer arrangement, it is not even possible to produce all the adjustment devices. A plurality of parameters must furthermore be set, which leads to highly complex adjustment.

Another possibility is to use an array transducer instead of a plurality of individual transducers. With appropriate driving of the array transducer, it is possible to implement different sound incidence directions and different focusing. A disadvantage is the much greater outlay for production and driving, for example electronics and signal processing, of an array transducer in comparison with the individual transducer. 2-Dimensional setting of the sound incidence direction requires a 2D array transducer, which is usually impracticable owing to the high number of elements. For arrangements of different types of individual transducers—for example different frequency—another disadvantage is that they cannot be replaced by a common array transducer, i.e. this would entail a corresponding number of array transducers and corresponding outlay.

SUMMARY

According to various embodiments, a nondestructive material testing device and a nondestructive material testing method can be provided with which the aforementioned problems are avoided, i.e. in which a fixed holder device with a plurality of transducers can be used and precise positioning of all the sensors is achievable despite manufacturing tolerances and deviations during use.

According to an embodiment, a method of nondestructive material testing, may comprise the steps of:—a nondestructive material testing device having at least two transducers is used,—the transducers are used to emit beams for material testing, the transducers being arranged in a common holder device,—the holder device is moved by means of a swiveling system and/or a linear movement system along a trajectory curve over the surface of a workpiece to be tested, so that a scanning curve on the surface of the workpiece is scanned,—an offset value, which specifies an offset between the beam direction of the transducer and the scanning curve, is determined for each transducer,—an optimal alignment of the holder device, for which the offset of the transducers is optimized overall, is found from the offset values.

According to a further embodiment, a calibrating body can be used for determination of the offset values, the offset being found with the aid of its reflection of the beam. According to a further embodiment, a calibrating body can be used which has at least a part of a hollow-spherical, spherical, hollow-cylindrical or cylindrical surface. According to a further embodiment, in order to determine of the offset value for a transducer, an emission direction of the transducer can be determined by finding, for two distances of the transducer from the calibrating body, the linear displacement of the transducer for which the beam reflected by the calibrating body strikes the transducer. According to a further embodiment, the offset value can be found such that it specifies a lateral deviation, the lateral deviation indicating the deviation of the beam of the transducer from the scanning curve in a direction perpendicular to the scanning curve and perpendicular to the emission direction of the transducer. According to a further embodiment, the optimal alignment can be determined so that the mean square error of the lateral deviations is minimized. According to a further embodiment, a rectilinear trajectory can be used as the trajectory curve, and the optimal alignment is determined by means of linear regression.

According to another embodiment, a device for nondestructive material testing may have at least two transducers for emitting beams, wherein —the transducers are arranged in a common holder device,—the holder device can be moved by means of a swiveling system and/or a linear movement system along a trajectory curve over the surface of a workpiece to be tested, so that a scanning curve on the surface of the workpiece can be scanned,—an offset value, which specifies an offset between the beam direction of the transducer and the scanning curve, can be determined for each transducer,—an optimal alignment of the holder device, for which the offset of the transducers is optimized overall, can be determined from the offset values, —the holder device can be aligned so that the optimal alignment is achieved.

According to a further embodiment, the device may have a calibrating body for determination of the offset values, which has at least a part of a hollow-spherical, spherical, hollow-cylindrical or cylindrical surface. According to a further embodiment, the transducer may be an ultrasound transducer.

According to a further embodiment, the device may be configured for carrying out the above described method.

BRIEF DESCRIPTION OF THE DRAWINGS

Other advantages and details of the invention will be explained with the aid of the exemplary embodiment represented in the drawing, in which.

DETAILED DESCRIPTION

Figure 1:
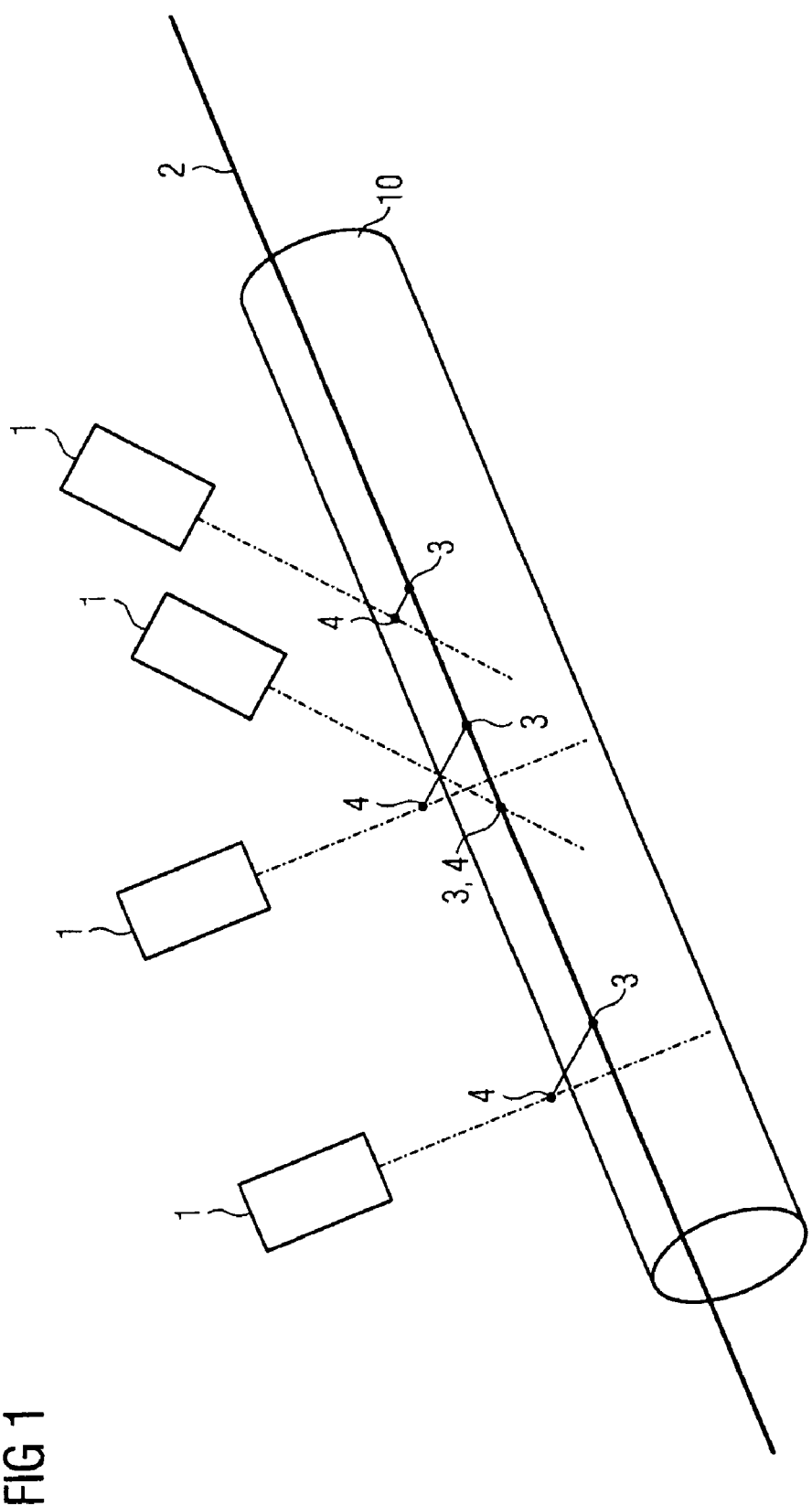
FIG. 1 schematically shows a scanning curve on a specimen and four ultrasound transducers.

In the nondestructive material testing method, a nondestructive material testing device having at least two transducers is used. The transducers are used to emit beams for material testing, and they are arranged in a common holder device. The holder device is moved by means of a swiveling system and/or a linear movement system along a trajectory curve over the surface of a workpiece to be tested, so that a scanning curve on the surface of the workpiece is scanned. An offset value, which specifies an offset between the beam direction of the transducer and the scanning curve, is furthermore determined for each transducer.

Lastly an optimal alignment of the holder device, for which the offset of the transducers is optimized overall, is found from the offset values. The optimal alignment is then expediently implemented in the holder device, for example by moving it into the optimal alignment. To this end, for example, a swiveling system may be provided for the holder device. The offset is in this case intended to mean the minimum distance of the beam of the transducer from the intended point of incidence or the intended line of incidence, the beam being considered in an idealized fashion without its broadening.

The nondestructive material testing device has at least two transducers for emitting beams. The transducers are arranged in a common holder device, and the holder device can be moved by means of a swiveling system and/or a linear movement system along a trajectory curve over the surface of a workpiece to be tested, so that a scanning curve on the surface of the workpiece can be scanned. For each transducer, an offset value which specifies an offset between the beam direction of the transducer and the scanning curve can be determined, and an optimal alignment of the holder device, for which the offset of the transducers is optimized overall, can be determined from the offset values. Lastly, the holder device can be aligned so that the optimal alignment is achieved. The alignment of the holder device may be carried out in an automated fashion, for example by means of a swiveling system, or manually.

The scanning curve is preferably an essentially rectilinear scanning curve. It is however also possible to use the invention with other scanning curves, for example circular trajectories.

The various embodiments ensure that the inaccuracies in the irradiation of the surface of a workpiece or specimen, caused by mechanical tolerances, are compensated for, and substantially more accurate testing is therefore carried out. The inspection results of a plurality of transducers can thereby be assigned precisely, and it furthermore allows the inspection time to be reduced by parallel inspection with a plurality of sound transducers, with high accuracy.

The transducer is preferably an ultrasound transducer, which represents a combination of an ultrasound emitter and a sensor for ultrasound. The device preferably has a multiplicity of the transducers. The invention may however also be used with other transducers such as optical sensors, in particular cameras or photodiodes, or even transducers which do not per se contain a sensor, for example lasers.

It is also possible to apply the invention to all the transducers of a holder device, i.e. to determine the offset for each transducer. As an alternative, only some of the transducers may be taken into account. This is advantageous when particularly high accuracy is required for only some of the transducers.

Advantageously, a calibrating body is provided for determination of the calibrating value. It preferably has a hollow-spherical or spherical surface, and thus in particular is a hollow hemisphere or a sphere. A hollow-cylindrical or cylindrical surface may also be used.

Preferably, in order to determine the offset value for a transducer, the precise emission direction of the transducer is determined by finding, for two distances of the transducer from the calibrating body, the linear displacement of the transducer for which the beam reflected by the calibrating body strikes the transducer.

Since the holder device is moved along the scanning curve when scanning a specimen, a position error in the direction of the scanning curve may preferably be compensated for by carrying out the measurement with this transducer earlier or later according to the speed of the scanning movement. A position error in the direction of the sound beam, or for optical sensors and also in general: in the direction of the sensor axis may be compensated for by taking into account the modified (sound) time of flight. For this, expediently it is merely necessary to assume that the position error is moderate enough so as not to depart from any focal range in respect of the distance, which can be assumed for conventional sound transducers. It is furthermore assumed that with a moderate angle error, the only perturbation is due to a displacement of the point of incidence resulting therefrom, but not the modified angle, which can be assumed for conventional sound transducers.

With these assumptions, it is sufficient for the lateral distance of the sound beams or sensor axes from the scanning curve at a particular position to achieve the value desired for the respective transducer. Sensors, for which a non-zero lateral offset is desired, may be displaced virtually on the scanning curve in order to simplify the following considerations.

According to an embodiment, the offset value is therefore found such that it specifies a lateral deviation, the lateral deviation specifying the deviation of the beam of the transducer from the scanning curve in a direction perpendicular to the scanning curve and perpendicular to the emission direction of the transducer.

The optimal alignment is preferably determined so that the mean square error of the lateral deviations is minimized, for example by means of linear regression for a rectilinear scanning curve.

The problem will be explained for a rectilinear scanning curve with the aid of FIG. 1. FIG. 1 shows four ultrasound transducers by way of example. These are fastened in a common holder (not shown) and emit sound in the direction of the surface of a cylindrical specimen 10. The holder is moved on the rectilinear scanning curve 2 for the scanning. In the ideal case, the sound beam of the ultrasound transducers 1 respectively strikes an ideal point of incidence 3, which lies precisely on the scanning curve 2 on the surface of the specimen 10. In practice, this will rarely be achieved owing to mechanical tolerances. In fact, the ultrasound transducers 1 emits past the scanning curve 2, a closest distance point 4 respectively being shown in FIG. 1. This reduces the accuracy of the testing.

According to a further embodiment, the actual path of sound beams is determined by means of a calibrator 5 in order to resolve the problem; those adjustable degrees of freedom which are available are established so as to set up a formula for the lateral offset of the sound beams relative to the scanning curve 2 as a function of the degrees of freedom, and solve this by an optimization method, for example regression. The degrees of freedom exist irrespective of whether they can be set automatically, for example by motors, or manually, for example through alignment and fixing by means of screws.

The latter, however, cannot be modified during operation. Typically available degrees of freedom are the positioning and alignment of the sensor holder. To this end, the following exemplary steps are carried out:

Step 1: Measuring the positions of the sound beams by means of a calibrator.

For the calibration, in this example, a calibrating body 5 having a hemispherical cavity 6 is used. Its shape echo, i.e. in general the echo on the surface, has the maximum amplitude when the sound beam passes through the center of the hemispherical cavity 6. In the case of laterally incident sound beams, there is a correspondingly lower echo amplitude.

The determination of the lateral position of a sound beam is performed by carrying out determination of the maximum echo amplitude position, by means of a search grid 7 which is aligned perpendicularly to the symmetry axis in the case of a cylindrically symmetrical calibrator 5—for an ultrasound transducer 1 oriented in the direction of the calibrator 5. Techniques may in this case also be used to increase the robustness in relation to measurement variations, for example smoothing. Techniques for increasing the resolution may also be employed, for example interpolation.

Step 2: Determining the spatial path of the sound beams.

Figure 2:
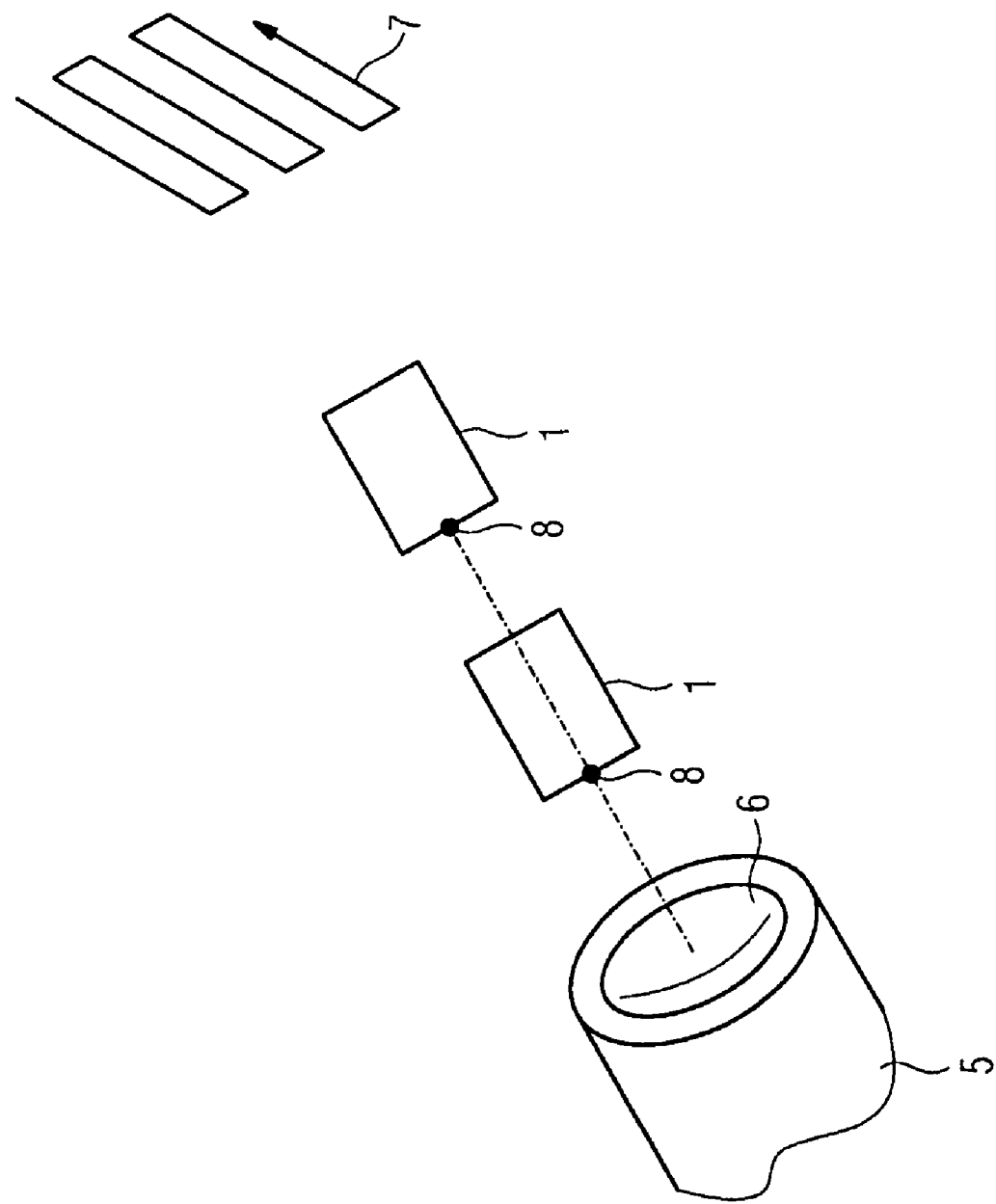
FIG. 2 schematically shows an ultrasound transducer and a hollow-spherical calibrating body.

The determination of the lateral position of the sound beam according to the first step is carried out for each sound transducer 1 at two different distances. In this way, two beam trajectory points 8 are determined according to FIG. 2. The spatial path of the sound beams is determined as a straight line through the two points 8 which are found.

Step 3: Calculating and minimizing the lateral offset error of the sound beams from the desired path The case of a rectilinear scanning curve 2 involves the parameters $x_0$, $y_0$ and $\alpha_{zy}$, $\alpha_{zx}$, i.e. the start point and angle for the best possible path of the scanning curve 2.

For example, minimization of the lateral offset error by linear regression is to be mentioned for the case of a rectilinear scanning curve 2, i.e. least-squares minimization of all the lateral offset errors. The parameters $x_0$, $y_0$ and $\alpha_{zy}$, $\alpha_{zx}$ are thereby determined. The following equations will for example be used for this, in which:

the points $A_i$ with the coordinates $(x_{Ai}, y_{Ai})$ and $B_i$ with the coordinates $(x_{Bi}, y_{Bi})$ are respectively two points of a measured beam direction of a transducer i, the parameters $x_0$, $y_0$ and $\alpha_{zy}$, $\alpha_{zx}$ specify the starting point and the path of the position of the scanning curve 2 which is desired, on the basis of being optimal, for the lateral offset of a transducer i:

The equation $$x_i(y_i) = x_{Ai} + (x_{Bi} - x_{Ai}) \cdot \frac{y_i - y_{Ai}}{y_{Bi} - y_{Ai}}$$

is equivalent to:

$$x_i(y_i) = y_i \cdot \frac{x_{Bi} - x_{Ai}}{y_{Bi} - y_{Ai}} + x_{Ai} - y_{Ai} \cdot \frac{x_{Bi} - x_{Ai}}{y_{Bi} - y_{Ai}}$$

For the following equations, $$k_{1i} = \frac{x_{Bi} - x_{Ai}}{y_{Bi} - y_{Ai}}$$

and $$k_{2i} = x_{Ai} - y_{Ai} \cdot \frac{x_{Bi} - x_{Ai}}{y_{Bi} - y_{Ai}}$$

For the position of the scanning curve 2 which is desired, on the basis of being optimal:

$$x_{0i} = \tan(\alpha_{zx}) \cdot z_i + x_0$$

$$y_{0i} = \tan(\alpha_{zy}) \cdot z_i + y_0$$

The lateral offset is:

$$e_i = x_i(y_{0i}) - x_{0i} = [k_{1i} \cdot z_i k_{1i} - z_i - 1] \cdot \begin{bmatrix} \tan(\alpha_{zy}) \\ y_0 \\ \tan(\alpha_{zx}) \\ x_0 \end{bmatrix} + k_{2i}$$

The above formula is equivalent to e=M*p−y, where:

$$p = \begin{bmatrix} \tan(\alpha_{zy}) \\ y_0 \\ \tan(\alpha_{zx}) \\ x_0 \end{bmatrix};$$

$$M = m_i = [k_{1i} \cdot z_i k_{1i} - z_i - 1];$$

$$y = -k_{2i};$$

For the least mean square error $$\sum_i e_i^2 = \min.$$

it follows that:

$$p = -(M^T \cdot M)^{-1} \cdot M^T \cdot y$$

Step 6: Setting the optimal parameters, for example alignment, distance and offset of the holder, automatically or manually. In the case of linear regression, this would mean that the holder is adjusted so that the calculated mean straight line lies exactly on the scanning curve.

What is claimed is:

1. A method of nondestructive material testing, comprising the steps of:
using a nondestructive material testing device having at least two transducers,
using the transducers to emit beams for material testing, the transducers being arranged in a common holder device,
moving the holder device by means of at least one of a swiveling system and a linear movement system along a trajectory curve over the surface of a workpiece to be tested, so that a scanning curve on the surface of the workpiece is scanned,
determining an offset value, which specifies an offset between the beam direction of the transducer and the scanning curve, for each transducer,
determining an optimal alignment of the holder device, for which the offset of the transducers is optimized overall, from the offset values,
wherein a calibrating body is used for determination of the offset values, the offset being found with the aid of its reflection of the beam, and
wherein determining the offset value for a transducer comprises determining an emission direction of the transducer by:
determining two beam trajectory points at two different distances between the calibrating body and the transducer, wherein each beam trajectory point is determined by adjusting the lateral position of the calibrating body relative to the transducer to find a location of maximum beam reflection at the calibrating body, and
calculating a straight line through the two determined beam trajectory points.

2. The method according to claim 1, wherein the calibrating body has at least a part of a hollow-spherical, spherical, hollow-cylindrical or cylindrical surface.

3. The method according to claim 1, wherein the offset value is found such that it specifies a lateral deviation, the lateral deviation indicating the deviation of the beam of the transducer from the scanning curve in a direction perpendicular to the scanning curve and perpendicular to the emission direction of the transducer.

4. The method according to claim 3, wherein the optimal alignment is determined so that the mean square error of the lateral deviations is minimized.

5. The method according to claim 4, wherein a rectilinear trajectory is used as the trajectory curve, and the optimal alignment is determined by means of linear regression.

6. A device for nondestructive material testing having at least two transducers for emitting beams, comprising:
a common holder device for holding the at least two transducers,
a swiveling system and/or a linear movement system for moving the common holder device along a trajectory curve over the surface of a workpiece to be tested, so that a scanning curve on the surface of the workpiece can be scanned,
a calibration system configured to:
utilize a calibrating body to determine an offset value for each transducer, which specifies an offset between the beam direction of the transducer and the scanning curve,
determine from the offset values an optimal alignment of the holder device, for which the offset of the transducers is optimized overall, and
determine an optimal alignment of the holder device for which the overall offset of the transducers is optimized, based on the determined offset values,
wherein determining the offset value for a transducer comprises determining an emission direction of the transducer by:
determining two beam trajectory points at two different distances between the calibrating body and the transducer, wherein each beam trajectory point is determined by adjusting the lateral position of the calibrating body relative to the transducer to find a location of maximum beam reflection at the calibrating body, and
calculating a straight line through the two determined beam trajectory points.

7. The device according to claim 6, wherein the transducer is an ultrasound transducer.

8. The device according to claim 6, wherein the calibrating body has at least a part of a hollow-spherical, spherical, hollow-cylindrical or cylindrical surface.

9. The device according to claim 6, wherein the offset value is found such that it specifies a lateral deviation, the lateral deviation indicating the deviation of the beam of the transducer from the scanning curve in a direction perpendicular to the scanning curve and perpendicular to the emission direction of the transducer.

10. The device according to claim 9, wherein the optimal alignment is determined so that the mean square error of the lateral deviations is minimized.

11. The device according to claim 10, wherein a rectilinear trajectory is used as the trajectory curve, and the optimal alignment is determined by means of linear regression.

* * * * *